(12) United States Patent
Mentzel et al.

(10) Patent No.: US 11,628,428 B2
(45) Date of Patent: *Apr. 18, 2023

(54) BIFUNCTIONAL CATALYST COMPRISING PHOSPHOROUS

(71) Applicant: Haldor Topsøe A/S, Kgs. Lyngby (DK)

(72) Inventors: Uffe Vie Mentzel, Vanløse (DK); Finn Joensen, Hørsholm (DK)

(73) Assignee: Topsoe A/S, Kgs. Lyngby (DK)

( * ) Notice: Subject to any disclaimer, the term of this patent is extended or adjusted under 35 U.S.C. 154(b) by 36 days.

This patent is subject to a terminal disclaimer.

(21) Appl. No.: 17/365,502

(22) Filed: Jul. 1, 2021

(65) Prior Publication Data

US 2021/0331147 A1 Oct. 28, 2021

Related U.S. Application Data

(62) Division of application No. 15/768,895, filed as application No. PCT/EP2016/079315 on Nov. 30, 2016, now Pat. No. 11,077,431.

(30) Foreign Application Priority Data

| Nov. 30, 2015 | (DK) | PA 2015 00766 |
| Nov. 30, 2015 | (DK) | PA 2015 00767 |
| Nov. 30, 2015 | (DK) | PA 2015 00768 |

(51) Int. Cl.

| *B01J 29/40* | (2006.01) |
| *C10G 3/00* | (2006.01) |
| *C07C 1/20* | (2006.01) |
| *B01J 27/14* | (2006.01) |
| *B01J 29/90* | (2006.01) |
| *C10G 35/00* | (2006.01) |
| *B01J 21/04* | (2006.01) |
| *B01J 29/85* | (2006.01) |
| *B01J 37/02* | (2006.01) |
| *B01J 37/08* | (2006.01) |
| *C07C 1/22* | (2006.01) |
| *B01J 37/28* | (2006.01) |
| *B01J 21/00* | (2006.01) |
| *B01J 35/00* | (2006.01) |
| *B01J 21/02* | (2006.01) |
| *C07C 43/04* | (2006.01) |
| *C07C 41/00* | (2006.01) |
| *C07C 41/01* | (2006.01) |
| *C07C 29/152* | (2006.01) |
| *C10G 50/00* | (2006.01) |
| *B01J 21/12* | (2006.01) |
| *B01J 23/00* | (2006.01) |
| *B01J 23/06* | (2006.01) |

(Continued)

(52) U.S. Cl.
CPC ........... *B01J 29/405* (2013.01); *B01J 21/005* (2013.01); *B01J 21/02* (2013.01); *B01J 21/04* (2013.01); *B01J 21/12* (2013.01); *B01J 23/005* (2013.01); *B01J 23/06* (2013.01); *B01J 27/14* (2013.01); *B01J 27/16* (2013.01); *B01J 29/40* (2013.01); *B01J 29/85* (2013.01); *B01J 29/90* (2013.01); *B01J 35/0006* (2013.01); *B01J 35/008* (2013.01); *B01J 35/0086* (2013.01); *B01J 35/0093* (2013.01); *B01J 37/0018* (2013.01); *B01J 37/0201* (2013.01); *B01J 37/024* (2013.01); *B01J 37/08* (2013.01); *B01J 37/088* (2013.01); *B01J 37/28* (2013.01); *C07C 1/20* (2013.01); *C07C 1/22* (2013.01); *C07C 29/152* (2013.01); *C07C 41/00* (2013.01); *C07C 41/01* (2013.01); *C07C 43/043* (2013.01); *C10G 3/45* (2013.01); *C10G 3/49* (2013.01); *C10G 35/00* (2013.01); *C10G 50/00* (2013.01); *C01B 2203/1211* (2013.01); *C01B 2203/1217* (2013.01); *C07C 2521/04* (2013.01); *C07C 2527/14* (2013.01); *C07C 2529/40* (2013.01); *C10G 2300/70* (2013.01); *C10G 2400/02* (2013.01); *C10G 2400/30* (2013.01); *Y02P 20/52* (2015.11); *Y02P 20/582* (2015.11); *Y02P 30/20* (2015.11)

(58) Field of Classification Search
CPC . B01J 29/40; B01J 29/405; B01J 29/90; B01J 29/85; B01J 21/02; B01J 21/04; B01J 21/12; B01J 21/005; B01J 23/005; B01J 23/06; B01J 27/14; B01J 27/16; B01J 35/0006; B01J 35/0086; B01J 35/008; B01J 35/0093; B01J 37/0018; B01J 37/08; B01J 37/088; B01J 37/024; B01J 37/28; B01J 37/0201; Y02P 20/53; Y02P 30/20; Y02P 20/52; Y02P 20/582; C10G 2300/70; C10G 2400/30; C10G 2400/02
USPC .................. 502/64, 69, 60, 71, 73, 77, 214
See application file for complete search history.

(56) References Cited

U.S. PATENT DOCUMENTS

| 5,877,368 A | 3/1999 | Kiyama |
| 6,156,689 A | 12/2000 | Kimble et al. |

(Continued)

FOREIGN PATENT DOCUMENTS

| CN | 1113649 A | 12/1995 |
| CN | 103406140 A | 11/2013 |

(Continued)

OTHER PUBLICATIONS

"Clean, Efficient and Sustainable Development and Utilization of Fossil Energy." The Second Chinese Academy of Engineering/National Energy Administration Energy Forum, Coal Industry Press, Beijing, China, 2012.

*Primary Examiner* — Elizabeth D Wood
(74) *Attorney, Agent, or Firm* — Blank Rome LLP

(57) ABSTRACT

A bifunctional catalyst for example for conversion of oxygenates, the bifunctional catalyst comprising zeolite, alumina binder, Zn and P, wherein Zn is present at least partly as $ZnAl_2O_4$.

11 Claims, No Drawings

(51) Int. Cl.
*B01J 37/00* (2006.01)
*B01J 27/16* (2006.01)

(56) References Cited

U.S. PATENT DOCUMENTS

| | | | |
|---|---|---|---|
| 6,489,528 | B2 | 12/2002 | Drake |
| 7,507,685 | B2 | 3/2009 | Ghosh et al. |
| 9,296,665 | B2 | 3/2016 | Kortan |
| 10,888,849 | B2 * | 1/2021 | Joensen .................. C10G 3/49 |
| 11,077,431 | B2 * | 8/2021 | Mentzel ................ C07C 29/152 |
| 2009/0071871 | A1 | 3/2009 | Joensen et al. |
| 2013/0165725 | A1 | 6/2013 | Chewter et al. |
| 2013/0261361 | A1 | 10/2013 | Blommel |
| 2014/0171691 | A1 | 6/2014 | Kortan et al. |
| 2015/0175897 | A1 | 6/2015 | Loveless et al. |
| 2015/0183694 | A1 | 7/2015 | Blommel |

FOREIGN PATENT DOCUMENTS

| | | |
|---|---|---|
| CN | 104039741 A | 9/2014 |
| CN | 104557416 A | 4/2015 |
| CN | 104557432 A | 4/2015 |
| EP | 0 671 212 A1 | 9/1995 |
| JP | 56-147727 A | 11/1981 |
| WO | WO 2007/020068 A1 | 2/2007 |

\* cited by examiner

BIFUNCTIONAL CATALYST COMPRISING PHOSPHOROUS

CROSS-REFERENCE TO RELATED APPLICATIONS

This is a divisional of U.S. application Ser. No. 15/768,895, filed Apr. 17, 2018, which is national stage of PCT/EP2016/079315, filed Nov. 30, 2016, which claims priority to Denmark Application No. PA 2015 00768, filed Nov. 30, 2015, Denmark Application No. PA 2015 00767, filed Nov. 30, 2015, and Denmark Application No. PA 2015 00766, filed Nov. 30, 2015, the entire disclosures of which are incorporated by reference herein.

FIELD OF THE INVENTION

Conversion of methanol to hydrocarbons over zeolite catalysts has been known for decades, and several variations of the process have been commercialized including MTG (methanol-to-gasoline), MTO (methanol-to-olefins), and MTP (methanol-to-propylene). In order to produce a physically robust catalyst, it is necessary to use a binder material. This binder is usually an oxide such as alumina, silica, magnesia etc.

BACKGROUND

A catalyst may be optimized to emphasize various functions such as product yield or selectivity. However, when one function is optimized the resulting catalyst will often show less advantageous with respect to other parameters. An example may be a catalyst optimized to achieve a higher product yield, but which then shows a decreased selectivity. Thus, a special task in developing new catalyst is to improve the catalyst on essential parameters without adverse effect to other important features.

SUMMARY OF THE INVENTION

In a first aspect of the present invention, a catalyst is provided which enables an improved aromatics yield.

In a second aspect of the present invention, a catalyst is provided which enables a reduced MeOH cracking to non-desired products such as CO and $CO_2$.

In a third aspect of the present invention is provided a catalyst which substantially regains activity after regeneration.

These and other advantages are achieved by a bifunctional catalyst for example for conversion of oxygenates and dehydrogenation of hydrocarbons, the catalyst comprising zeolite, alumina binder, zinc (Zn) and phosphorous(P), wherein the Zn is present at least partly as $ZnAl_2O_4$.

DETAILED DESCRIPTION

To increase the yield of aromatics, a bifunctional catalyst containing acidic zeolite sites as well as dehydrogenation sites e.g. metal or oxide is provided. This means that a stream comprising one or more oxygenates e.g. methanol may be converted in the presence of the catalyst into hydrocarbons rich in aromatics while dehydrogenation of hydrocarbons such as naphthenes, paraffins and/or isoparaffins, into olefins and/or aromatics also takes place.

In preferred embodiments, the catalyst is optimized for conversion of oxygenates such as methanol and/or dimethyl ether (DME) into aromatics (herein abbreviated MTA).

The presence of P in the zeolites leads to improved steam resistance, leading to a longer ultimate lifetime of the catalyst. Furthermore, the applicant has discovered that the presence of P in a Zn/ZSM-5 catalyst system leads to significantly lower methanol cracking activity. This is a surprising and very important effect, since cracking of methanol to carbon oxides is a highly undesired side reaction in MTA.

Depending on the production process, the P in the catalyst may be present in various concentrations in both binder and zeolite of the present catalyst. E.g. in some embodiments the P concentration may be higher in the binder phase than in the zeolite phase which for example may be the case when P is applied by impregnation.

P may in several advantageous embodiments be present as oxide or hydroxide species, e.g. as phosphoric acid, phosphates, such as $H_2PO_4^-$, $HPO_4^{2-}$ or $PO_4^{3-}$, or as phosphorous oxides, e.g., $P_2O_5$. P may also be present as aluminum phosphate and/or zinc phosphate.

The catalyst may contain various amounts of Zn and P. The content of P and Zn in the catalyst expressed as wt % P/wt % Zn may for example be 1/10, 2/10, 4/10, 1/5, 2/5, 1/3, 3/3 or 5/3. Furthermore, the molar ratio of P/Zn in the catalyst may be within the range 0.01-5, 0.02-2 or 0.05-1. The amounts of Zn and P in the catalyst affect the activity of the catalyst in terms of selectivity towards aromatics as well as the activity in methanol cracking to carbon oxides. As described herein, the concentration of free ZnO in the binder phase is very low in several preferred embodiments of the catalyst. A catalyst containing Zn as well as $Al_2O_3$ and P is particularly desirable due to the combined effect of spinalization and presence of P, leading to a very low methanol cracking activity.

The binder may be a pure alumina binder or an alumina-based binder further comprising mixtures of aluminum oxide and aluminum hydroxide and/or e.g. silica/alumina.

The zeolite may for example be one of the commonly known zeolites used in MTA and MTG processes. For example, H-ZSM-5 may be a preferred zeolite for the present catalyst due to its unique pore structure leading to favorable size selectivity as well as its relatively low coking rate. H-ZSM-5 may be particularly preferred in case of MTA processes.

Examples of Zn/ZSM-5 catalysts with low content of Zn such as 1% Zn for MTA are known and it has been argued that higher Zn % is to be avoided in order to avoid methanol cracking to carbon oxides. However, the applicant has shown that a high Zn content in the catalyst may result in an improved aromatics yield in MTA processes compared to known catalysts. Thus, in several advantageous embodiments the total Zn content in the catalyst is 3-25 wt %, 5-20 wt %, 7-15 wt % or 8-13 wt %, such as more than 7 wt % Zn, more than 10 wt % Zn or 12 wt % or more Zn.

Depending on the production process the Zn and P in the catalyst may be present in various concentrations in both binder and zeolite of the present catalyst. E.g. in some embodiments the Zn concentration is higher in the binder phase than in the zeolite phase which for example may be the case where the Zn is applied by impregnation.

A catalyst wherein Zn and/or P is present in both zeolite and alumina binder allows for industrial production by "simple" means such as by impregnation. For example, a bifunctional catalyst as herein described may be achieved by Zn and/or P impregnation of a "base catalyst" comprising an alumina binder and a zeolite such as ZSM-5. A preferred base catalyst comprises 30-50% binder and 50-70% zeolite.

The impregnation may be carried out by contacting the zeolite or the zeolite and alumina binder with a Zn— and/or P-containing solution. The solution may preferably be aqueous, but other solvents than water may be preferred as well. An example of a preferred impregnation solution is zinc nitrate dissolved in aqueous phosphoric acid. Zn and/or P may also be applied by contacting the zeolite or the zeolite and alumina binder with one or more solid Zn and/or P compounds, e.g., by mixing and/or grinding or other treatments to ensure intimate mixing of the components.

The Zn source may be any Zn-containing, organic and/or inorganic, compound. Preferred compounds comprise zinc nitrate, zinc acetate, zinc oxide, zinc hydroxide, zinc carbonate or mixtures hereof. Examples of preferred P sources include phosphoric acid, phosphorous oxide/hydroxide species as well as triammoniumorthophosphate, diammoniumhydrogenphosphate, ammoniumdihydrogenphosphate or mixtures thereof. Mixed Zn—P compounds, such as zinc orthophosphates or -pyrophosphates may also by preferred. Zn and P can be applied simultaneously to the catalyst in a very simple manner by impregnation of a base catalyst with a solution containing Zn as well as P, followed by calcination. The catalyst can also be prepared by impregnation of P onto a catalyst containing Zn, or by impregnation of Zn onto a catalyst containing P.

In order to provide a functional catalyst, the addition of Zn and P containing species (either by impregnation of a liquid or by mixing/grinding of solids), will typically be followed by calcination or similar treatment(s).

However, when an alumina/zeolite based catalyst is impregnated with Zn and P in order to obtain the desired amount of Zn and P in the zeolite significant amounts of Zn and P species may also deposit in the binder phase, for example, as phosphorous oxide/hydroxide (phosphates), ZnO and/or $ZnAl_2O_4$. Various ratios of $ZnO/ZnAl_2O_4$ in the binder may be achieved depending on the treatment of the impregnated catalyst. Furthermore, P may bind to Zn and alumina in the binder phase as well as in the zeolite phase.

The applicant has shown that in desirable embodiments of the catalyst Zn in the alumina binder is present mainly as $ZnAl_2O_4$. Defining the relative amount of zinc oxide, ZnO, in the binder phase as molar percentage of Zn present as ZnO relative to the total amount of Zn contained in the binder phase it may be desirable to have a catalyst where the amount of ZnO present in the binder phase as less than 50%, or preferably less than 10%, such as less than 5% or less than 2%, preferably less than 1%, such as 0.5% or less than 0.1% ZnO.

It may be preferred that the Zn in the binder has been fully spinelized, according to the reaction equation $ZnO+Al_2O_3 \rightarrow ZnAl_2O_4$, meaning that all or substantially all of the Zn in the binder is present as $ZnAl_2O_4$.

Zn may also be present as zinc phosphate in the binder and/or zeolite phase. In a spinelized catalyst, with a high $ZnAl_2O_4/ZnO$ ratio, small amounts of ZnO may be eliminated by reaction with phosphorous species to form zinc phosphate. The zinc phosphate may be amorphous and thus not detectable in XRD analysis.

Preferably a large part of the Zn in the alumina binder is present as $ZnAl_2O_4$. Defining the relative amount of $ZnAl_2O_4$ in the binder phase as molar percentage of Zn present as $ZnAl_2O_4$ relative to the total amount of Zn contained in the binder phase, in some embodiments 50-100% of the Zn in the binder is present as $ZnAl_2O_4$, for example more than 60%, more than 70% or more than 80%.

In some advantageous embodiments 85-100% of the Zn in the binder is present as $ZnAl_2O_4$, such as more than 90% or more than 95%.

As shown by the applicant cracking of MeOH may be avoided with a high degree of spinelization, it may be preferred, especially in case of a high Zn content in the catalyst, that more than 97% of the Zn in the binder is present as $ZnAl_2O_4$, such as more than 98%, more than 99%, more than 99.5% or more than 99.8% of the Zn in the binder is present as $ZnAl_2O_4$. Optimal and practically achievable $ZnAl_2O_4$ content ranges may be 95-100% in the binder is present as $ZnAl_2O_4$, such as 97%-99.9% Zn in the binder is present as $ZnAl_2O_4$.

In preferred embodiments the catalyst has been fully spinelized meaning that all or substantially all of the Zn in the binder is present as $ZnAl_2O_4$.

ZnO in the binder is active in cracking methanol which is an undesired reaction in MTA. Depending on the means of production and after-treatment of the catalyst more or less of the Zn in the alumina binder may be present as $ZnAl_2O_4$. Steaming or calcination of a Zn impregnated catalyst as commonly applied in production of metal/zeolite systems may result in a partial spinelization of the $Zn(ZnO+Al_2O_3 \rightarrow ZnAl_2O_4)$. However, it has been shown that with a high Zn content even a relatively high degree of spinelization may lead to substantial MeOH cracking, but that a very desirable catalyst is achieved with a high degree of or preferably full spinelization of Zn in the alumina binder i.e. where all or substantially all of Zn in the binder is present as $ZnAl_2O_4$.

A bifunctional catalyst where all of or substantially all of Zn is present as $ZnAl_2O_4$ where substantially no ZnO is present in the binder as described herein exhibits a low selectivity to $CO_x$ even if the Zn content is high e.g. above 9 wt %. Thus, in preferred embodiments the fresh (start of run) catalyst has a $CO_x$ selectivity (determined at 420° C., 20 bar, 10 mol % methanol and a WHSV of 1.6) below 8% preferably below 7% such as 6% or below, or 5% or lower, or even 2% or lower. The $CO_x$ selectivity is defined as the molar percentage of methanol in the feed converted into CO and $CO_2$ according to the net reactions:

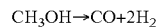

$$CH_3OH \rightarrow CO + 2H_2$$

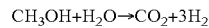

$$CH_3OH + H_2O \rightarrow CO_2 + 3H_2$$

Thus, according to some embodiments of the present application is provided a preferred bifunctional catalyst comprising alumina binder, H-ZSM-5 and 8-15 wt % Zn in the total catalyst and where the Zn in the binder is fully or substantially fully spinelized. Said catalyst provides a high aromatics yield in a MTA reaction while cracking of the methanol is reduced to below 7%.

An exemplary bifunctional catalyst may desirably comprise 30-65 wt % H-ZSM-5, 1-40 wt % $ZnAl_2O_4$, 0-40 wt % $AlPO_4$, 0-40 wt % $Al_2O_3$, 0-10 wt % ZnO.

The catalyst may further in some embodiments be characterized by having 0.1-12 wt % such as 1-7 wt % Zn present in the zeolite phase.

Alternatively, various embodiments of the catalyst may comprise 50-60 wt % H-ZSM-5, 10-35 wt %, 0-30% $AlPO_4$, 2-25 wt % $Al_2O_3$, 0-7 wt % ZnO. In order to avoid the presence of free ZnO in the binder phase, it may be beneficial to have at least a small excess of $Al_2O_3$ which is not spinelized in reaction with ZnO. Using a higher amount of $Al_2O_3$ in the preparation of the "base catalyst" will lead to a more robust catalyst preparation process.

Due to gradual coking of the catalyst during operation the catalyst must be regenerated at intervals in a stream comprising $O_2$.

A partially spinelized catalyst with a moderate to high $ZnAl_2O_4$ content may e.g. be obtained by heating the Zn-impregnated base catalyst at 300-500° C. in air.

A partially spinelized catalyst with a very high $ZnAl_2O_4$ content, fully spinelized catalyst or a substantially fully spinelized catalyst may be obtained by heating the Zn impregnated base catalyst at 300-550° C. in steam or in an atmosphere comprising at least 10 vol %, 30 vol % 50 vol % or 80 vol % steam.

A partially spinelized catalyst with a very high molar $ZnAl_2O_4$:$ZnO$ ratio, fully spinelized catalyst or a substantially fully spinelized catalyst may be obtained by heating a partially spinelized catalyst at 300-550° C. in steam or in an atmosphere comprising at least 10 vol %, 30 vol % 50 vol % or 80 vol % steam.

An at least partially spinelized catalyst, preferably a partially spinelized catalyst with a very high $ZnAl_2O_4$:$ZnO$ ratio, fully spinelized catalyst or a substantially fully spinelized catalyst as described herein may be provided in numerous ways including obtaining a desired spinelized catalyst during production or by producing a catalyst with a spinelization degree below the desired spinelization percentage and followed by steaming said catalyst in a subsequent step e.g. as in an in situ steaming step to obtain a catalyst with a desired degree of spinelization.

Thus, according to the present application is provided a bifunctional catalyst based on an alumina based binder and a zeolite, where said catalyst in various advantageous embodiments comprises a relatively high Zn content (such as 7-15% e.g 10 or 12 wt %) and P (e.g. in an amount where Zn/P>1) and where Zn in the alumina binder has been spinelized to a degree where COx selectivity is lower than a desired value (e.g. lower than 5% or even lower than 2%). Zn and P in the catalyst may be present as a number of different components in binder and zeolite phase depending on amount of Zn and P as well as treatment of the catalyst.

Various methods may be applied to produce the bifunctional catalyst: The three components (P, Zn and Zeolite) may constitute an integrated entity, e.g. as obtained by introducing the Zn and/or P components by impregnation or ion-exchange to the zeolite, either onto the zeolite itself or onto an extrudate in which the zeolite is embedded in an alumina binder. The Zn and/or P component may also be added in the form of a solid species such as an oxide, hydroxide or carbonate together with the zeolite, binder and/or lubricants prior to shaping, e.g. during mixing, extrusion or pelletization.

The post-impregnation treatment (calcination or similar heat treatment) is preferably carried out in a humid atmosphere, e.g., by heating the Zn—P impregnated base catalyst at 300-550° C. in steam or in an atmosphere comprising at least 10 vol %, 30 vol % 50 vol % or 80 vol % steam.

Also physical mixtures of several zeolites and metal components may be applied and the mixture may be charged to the reactor to form a uniform mixture or to form alternating layers or they may be graded to various degrees.

Thus, there is provided a
method for producing a bifunctional catalyst comprising an alumina binder, zeolite, P and Zn, said method comprising the steps of
impregnating an alumina/zeolite catalyst with a P and/or Zn-containing liquid solution
at least partly spinelizing the Zn impregnated alumina/zeolite catalyst by heating the impregnated alumina/zeolite catalyst to 300-650° C. for 0.25-7 h.

method for producing a bifunctional catalyst comprising an alumina binder, zeolite, P and Zn, said method comprising the steps of
impregnating a Zn and/or P compound or a solution of a Zn and/or P compound onto a zeolite or alumina/zeolite by mixing
shaping said mixture by extrusion or pelletization
at least partly spinelizing the Zn impregnated alumina/zeolite catalyst by heating the impregnated alumina/zeolite catalyst to 300-650° C. for 0.25-7 h.

Advantageously the present bifunctional catalyst may be used in a methanol conversion process comprising
a conversion step wherein a feed stream comprising oxygenates such as methanol and/or DME is converted into a hydrocarbon stream rich in aromatics
a separation step wherein the hydrocarbon stream rich in aromatics is separated into at least an aromatics rich product stream, stream comprising water and a recycle stream.

According to the present application is also provided a process for conversion of a feed stream comprising methanol and/or DME to a aromatics rich hydrocarbon stream in presence of a bifunctional catalyst comprising Zn and P, wherein the aromatics rich hydrocarbon stream is separated into at least an aromatics rich product stream, a process condensate stream and an off gas stream, and where at least part of said off gas stream is recycled. In the process preferably $H_2$ is at least partly removed from the off gas recycle. The process may for example be an MTA or an MTG process.

If a partially spinelized bifunctional catalyst is provided for the process, the process may advantageously comprise an initial step wherein the partially spinelized catalyst is further purposively spinelized in situ by passing steam through the catalyst bed at elevated temperature. For example, the partially spinelized bifunctional catalyst may be steamed in situ in on or more steps in order to provide a fully or substantially fully spinelized catalyst which hereafter is used for conversion of a feed stream comprising methanol and/or DME to an aromatics rich hydrocarbon stream.

In preferred embodiments of the process the bifunctional catalyst is a bifunctional catalyst as described herein.

EXAMPLE 1

Preparation of Catalyst

A base catalyst containing 65 wt % H-ZSM-5 and 35% $Al_2O_3$ was prepared by mixing followed by extrusion following well known procedures. Upon calcination, samples of the base catalyst were impregnated with an aqueous solution containing zinc nitrate at different Zn concentrations. The resulting pore-filled extrudates were heated to 470° C. in air and kept at 470° C. for 1 h to obtain catalysts with various amounts of Zn.

EXAMPLE 2

Catalyst Activity and Regeneration

Catalysts prepared by the procedure described in example 1 were subjected to conversion of methanol at 420° C. in an isothermal fixed bed reactor. $N_2$ was used as an inert co-feed to obtain a methanol concentration of 7 mol % in the reactor inlet. The total pressure was 20 bar, and the space velocity (WHSV) of methanol was 2 h$^{-1}$.

Zn/H-ZSM-5 catalysts suffer from reversible as well as irreversible deactivation. Deposition of carbon (coke) on the catalyst is responsible for reversible deactivation. In the example shown in table 1, the deactivated (coked) catalyst is regenerated by removal of the deposited carbon by combustion in a flow of 2% $O_2$ (in $N_2$) at 500° C.

Due to irreversible deactivation, the catalyst did not fully regain its activity after regeneration. The results in table 1 show, that a catalyst containing 10% Zn is able to regain significantly more of its original activity after regeneration than a catalyst containing 5% Zn.

TABLE 1

Catalyst activity after regeneration. Wt % of aromatics in hydrocarbon product is defined as the mass of aromatics relative to the total mass of hydrocarbons in the effluent stream.

| Zn content (wt %) | Aromatics in total hydrocarbon product (wt %) | Percentage of aromatics selectivity regained after regeneration |
|---|---|---|
| 5 | 52 | 90 |
| 10 | 51 | 95 |

EXAMPLE 3

Stability Towards Steaming

To simulate catalyst activity after extended operation under industrial conditions, the catalysts were subjected to methanol conversion after steaming under severe conditions. Methanol conversion was performed under the same conditions as in example 2. The results in Table 2 show that the catalyst containing 10% Zn retains significantly more of its original activity than the catalyst containing 5 wt % Zn after severe steaming.

TABLE 2

Loss of catalyst activity upon severe steaming (100% steam for 48 h at 500° C. and 1 bar). Wt % of aromatics in hydrocarbon product is defined as the mass of aromatics relative to the total mass of hydrocarbons in effluent stream.

| Zn content (wt %) | Aromatics in hydrocarbon product (wt %), fresh catalyst | Aromatics (wt %) in hydrocarbon product, steamed catalyst |
|---|---|---|
| 5 | 52 | 28 |
| 10 | 51 | 36 |

EXAMPLE 4

Methanol Cracking vs. Zn Content

Cracking (decomposition) of methanol/DME can occur via several mechanisms. For example, the acidic sites in the catalyst may catalyze cracking of DME to $CH_4$, CO, and $H_2$, while certain Zn species catalyze cracking of methanol to CO and $H_2$. $CO_2$ can be formed as a primary cracking product or indirectly via the water gas shift reaction.

When methanol is converted over a catalyst containing Zn, part of the methanol is converted to $CO_x$ due to cracking, which results in lower yield of hydrocarbon products. Methanol conversion has been performed at 420° C., 20 bar, 10 mol % methanol (N2 balance), and a space velocity (WHSV) of 1.6.

The results in Table 3 were obtained using catalysts prepared according to example 1. The results show that the cracking activity is highly dependent on the amount of Zn, i.e. higher Zn content leads to higher cracking activity.

TABLE 3

$CO_x$ selectivity at different contents of Zn

| Zn content (wt %) | $CO_x$ selectivity (%) |
|---|---|
| 0 | <0.1 |
| 3 | 2 |
| 5 | 4 |
| 10 | 9 |

EXAMPLE 5

$CO_x$ Selectivity After Calcination and Steaming

A base catalyst containing 65% ZSM-5 and 35% $Al_2O_3$ was impregnated with aqueous zinc nitrate solution. The resulting pore filled extrudates were calcined in air and steam, respectively. Furthermore, the catalyst calcined in air was subjected to steaming after calcination. Methanol conversion over these catalysts was performed using the same conditions as in example 4.

The results in table 4 show that the presence of steam during calcination of the impregnated catalyst or heating the catalyst in the presence of steam after calcination leads to lower selectivity to $CO_x$. This observation may be rationalized by the fact that the presence of steam leads to formation of $ZnAl_2O_4$ rather than free ZnO in the binder phase.

TABLE 4

$CO_x$ selectivity for catalysts containing 10% Zn, calcined in the presence of different amounts of steam

| Condition | $CO_x$ selectivity (%) |
|---|---|
| Calcined in air | 9 |
| Calcined in steam (500° C., 2 h) | 2 |
| Calcined in air, steamed after calcination (500° C., 5 h) | 4 |
| Calcined in air, steamed after calcination (500° C., 48 h) | <0.1 |

EXAMPLE 6

Preparation of Catalyst Comprising P

A base catalyst containing 65 wt % H-ZSM-5 and 35% $Al_2O_3$ was prepared by mixing followed by extrusion following well known procedures. Upon calcination, samples of the base catalyst were impregnated with an aqueous solution of zinc nitrate and phosphoric acid. The resulting pore-filled extrudates were heated to 470° C. and kept at 470° C. for 1 h to obtain catalysts with 10 wt % Zn and 0, 1 and 3 wt % P, respectively.

EXAMPLE 7

Stability Towards Steaming

To simulate catalyst activity after extended operation under industrial conditions, the catalysts of example 6 were subjected to methanol conversion after steaming under severe conditions. Methanol conversion has been performed at 420° C., 20 bar, 10 mol % methanol (N2 balance), and a space velocity (WHSV) of 1.6. The results in Table 5 show that the catalysts containing P retains significantly more of the original activity than the catalyst without P, resulting in a higher yield of aromatics.

TABLE 5

Loss of catalyst activity upon severe steaming (100% steam for 48 h at 500 C. and 1 bar). Wt % of aromatics in hydrocarbon product is defined as the mass of aromatics relative to the total mass of hydrocarbons in the effluent stream. All catalysts contain 10 wt % Zn.

| P content (wt %) | Atomic P/Zn ratio in the catalyst | Aromatics in hydrocarbon product (wt %), fresh catalyst | Aromatics (wt %) in hydrocarbon product, steamed catalyst |
|---|---|---|---|
| 0 | 0 | 51 | 36 |
| 0.8 | 0.2 | 51 | 41 |
| 2.3 | 0.5 | 55 | 42 |

EXAMPLE 8

Methanol Cracking vs. P Content

The results in Table 6 were obtained using catalysts prepared according to example 6, with 10% Zn and different amounts of P. Methanol conversion was performed under the same conditions as in example 7. The results show that the cracking activity is suppressed when P is present in the catalyst. Noticeably, the catalyst containing a low amount of P (0.8 wt %), thus having a low atomic P/Zn ratio (0.2), showed the same activity in methanol cracking as the catalyst without P. On the other hand, the catalyst containing a higher amount of P (2.3 wt %), thus having a higher atomic P/Zn ratio (0.5), shows significantly lower activity for methanol cracking, i.e. formation of CO and $CO_2$, indicating that a certain minimum amount of P is needed in order to suppress methanol cracking. The desired amount of P may depend on the Zn concentration.

TABLE 6

$CO_x$ selectivity for fresh catalysts containing 10% Zn and different amounts of P

| P content (wt %) | Atomic P/Zn ratio in the catalyst | $CO_x$ selectivity (%) |
|---|---|---|
| 0 | 0 | 9 |
| 0.8 | 0.2 | 9 |
| 2.3 | 0.5 | 2.5 |

The invention claimed is:

1. A bifunctional catalyst comprising a ZSM-5 or ZSM-11 zeolite, an alumina binder, Zn and P, wherein the Zn and P is present throughout the catalyst in both the binder and the zeolite, the catalyst has a total Zn content of more than 7 wt %, at least 95% of the Zn in the binder is present as $ZnAl_2O_4$ and the molar amount of Zn present in the binder phase as ZnO is less than 5% relative to the total amount of Zn present in the binder, the molar ratio of Zn/P is greater than 1, the alumina binder is a pure alumina binder or an alumina-based binder comprising mixtures of aluminum oxide and aluminum hydroxide and/or silica alumina, and wherein the Zn in the alumina binder is fully or partly spinelized.

2. A bifunctional catalyst according to claim 1, wherein the catalyst is an extruded or pelletized catalyst.

3. A bifunctional catalyst according to claim 1, comprising 30-65 wt % zeolite, 1-40 wt % $ZnAl_2O_4$, up to 40 wt % $Al_2O_3$, and up to 10 wt % ZnO.

4. A bifunctional catalyst according to claim 1, wherein the alumina binder further comprises silica.

5. A bifunctional catalyst according to claim 1, wherein the catalyst, by X-ray diffraction, does not contain free ZnO in the binder.

6. A bifunctional catalyst according to claim 1, wherein the total Zn content is 7-25 wt % in the catalyst.

7. A bifunctional catalyst according to claim 1, wherein the molar amount of Zn present in the binder as $ZnAl_2O_4$ constitutes at least 99% of the total amount of Zn present in the binder.

8. A bifunctional catalyst according to claim 1, wherein the Zn in the zeolite is present as ZnO, Zn(OH)+ and/or Zn++ in ion exchange positions.

9. A bifunctional catalyst according to claim 1, wherein the total Zn content in the catalyst is 8-15 wt % Zn.

10. A bifunctional catalyst according to claim 1, wherein the Zn content in the binder is substantially the same regardless of whether the catalyst is in a fully or partly spinelized form.

11. A bifunctional catalyst according to claim 10, wherein the fully spinelized form is obtained by heating a partly spinelized form at 300-550° C. in an atmosphere comprising steam.

* * * * *